(12) United States Patent
Giridhar et al.

(10) Patent No.: US 6,399,775 B1
(45) Date of Patent: Jun. 4, 2002

(54) METHODS FOR THE PREPARATION OF POLYMORPHS OF DOXAZOSIN MESYLATE

(76) Inventors: Thota Giridhar; Reguri Buchi Reddy; Chakka Ramesh, all of 7-1-27, Ameerpet, Hyderabad, Andhra Pradesh (IN)

( * ) Notice: Subject to any disclaimer, the term of this patent is extended or adjusted under 35 U.S.C. 154(b) by 0 days.

(21) Appl. No.: 09/615,241

(22) Filed: Jul. 13, 2000

(51) Int. Cl.⁷ .............................................. C07D 405/14
(52) U.S. Cl. ....................................................... 544/291
(58) Field of Search .......................................... 544/291

*Primary Examiner*—Mark L. Berch
*Assistant Examiner*—Kahsa Habte
(74) *Attorney, Agent, or Firm*—Ladas & Parry

(57) ABSTRACT

Form D of doxazosin mesylate and a process for preparing Form D of doxazosin mesylate is described. The process is (a) dissolving doxazosin base and methane sulfonic acid in an alcohol having 1 to 8 carbon atoms; (b) precipitating Form D of doxazosin mesylate from the resulting solution; and (c) separating the Form D of doxazosin mesylate.

2 Claims, 15 Drawing Sheets

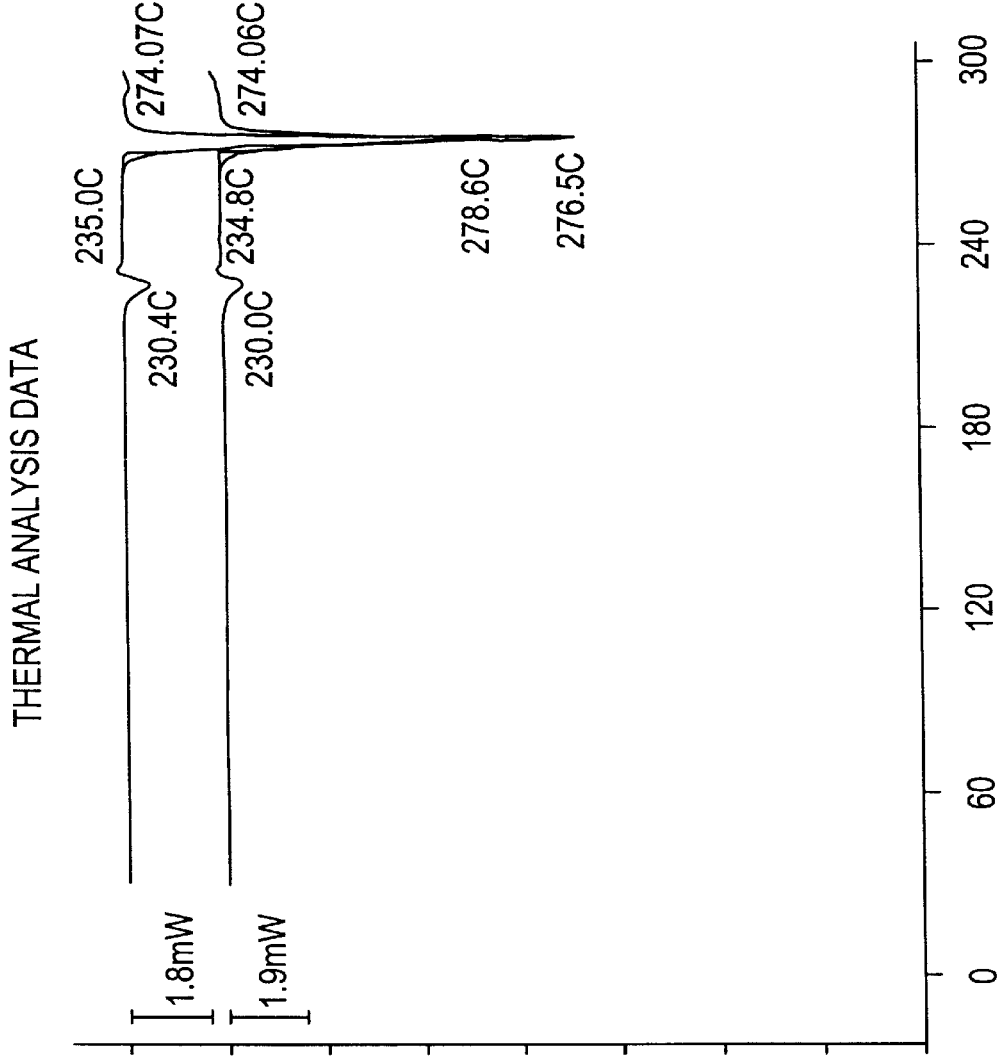

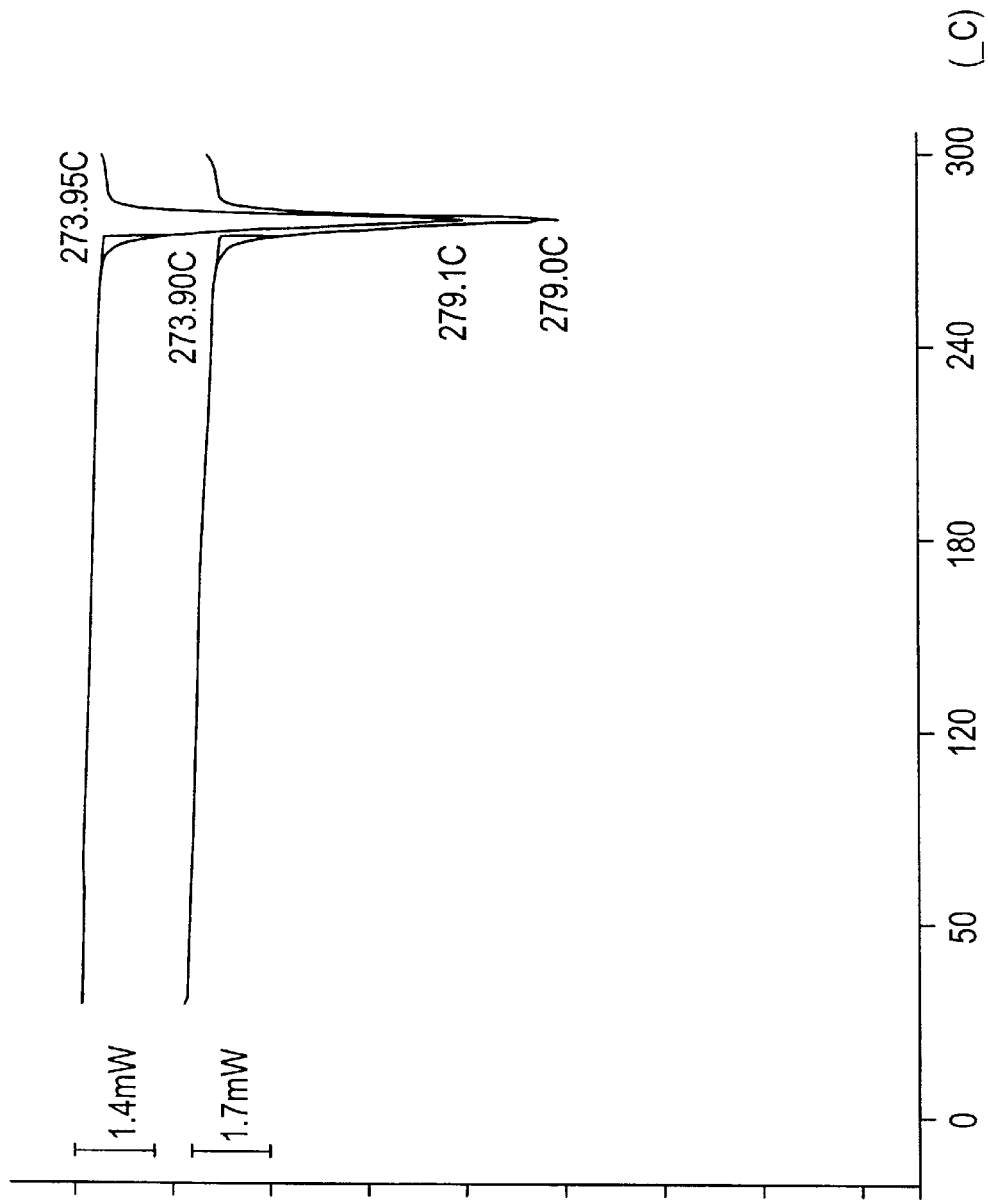

FIG. 3C

| Peak No. | 2Theta | FWHM | d-value | Intensity | I/Io |
|---|---|---|---|---|---|
| 1 | 5.740 | 0.188 | 15.3841 | 1951 | 100 |
| 2 | 9.380 | 0.165 | 9.4207 | 204 | 10 |
| 3 | 11.160 | 0.188 | 7.9218 | 595 | 31 |
| 4 | 11.520 | 0.188 | 7.6750 | 498 | 26 |
| 5 | 13.560 | 0.141 | 6.5246 | 84 | 4 |
| 6 | 14.140 | 0.165 | 6.2583 | 397 | 20 |
| 7 | 14.440 | 0.188 | 6.1289 | 352 | 18 |
| 8 | 15.080 | 0.118 | 5.8702 | 92 | 5 |
| 9 | 15.200 | 0.118 | 5.8241 | 110 | 6 |
| 10 | 16.700 | 0.118 | 5.8042 | 220 | 11 |
| 11 | 17.060 | 0.188 | 5.1931 | 596 | 31 |
| 12 | 17.820 | 0.235 | 4.9733 | 1618 | 83 |
| 13 | 18.380 | 0.235 | 4.8230 | 482 | 24 |
| 14 | 18.780 | 0.141 | 4.7212 | 147 | 8 |
| 15 | 19.140 | 0.235 | 4.6332 | 225 | 12 |
| 16 | 19.620 | 0.141 | 4.5209 | 142 | 7 |
| 17 | 20.760 | 0.235 | 4.2752 | 1336 | 68 |
| 18 | 21.560 | 0.235 | 4.1183 | 257 | 13 |
| 19 | 21.760 | 0.118 | 4.0809 | 306 | 16 |
| 20 | 22.080 | 0.141 | 4.0225 | 265 | 14 |
| 21 | 22.260 | 0.118 | 3.9904 | 252 | 13 |
| 22 | 23.120 | 0.118 | 3.8438 | 232 | 12 |
| 23 | 23.260 | 0.141 | 3.8210 | 249 | 13 |
| 24 | 23.720 | 0.141 | 3.7479 | 217 | 11 |
| 25 | 24.280 | 0.235 | 3.6628 | 800 | 41 |
| 26 | 25.460 | 0.212 | 3.4956 | 106 | 5 |
| 27 | 25.660 | 0.141 | 3.4688 | 122 | 6 |
| 28 | 25.920 | 0.118 | 3.4346 | 96 | 5 |
| 29 | 26.580 | 0.282 | 3.3508 | 651 | 33 |
| 30 | 28.120 | 0.165 | 3.1707 | 202 | 9 |
| 31 | 28.480 | 0.118 | 3.1314 | 136 | 7 |
| 32 | 28.660 | 0.212 | 3.1122 | 105 | 5 |
| 33 | 29.620 | 0.141 | 3.0134 | 95 | 5 |
| 34 | 29.840 | 0.141 | 2.9917 | 132 | 7 |
| 35 | 31.320 | 0.118 | 2.8537 | 92 | 5 |

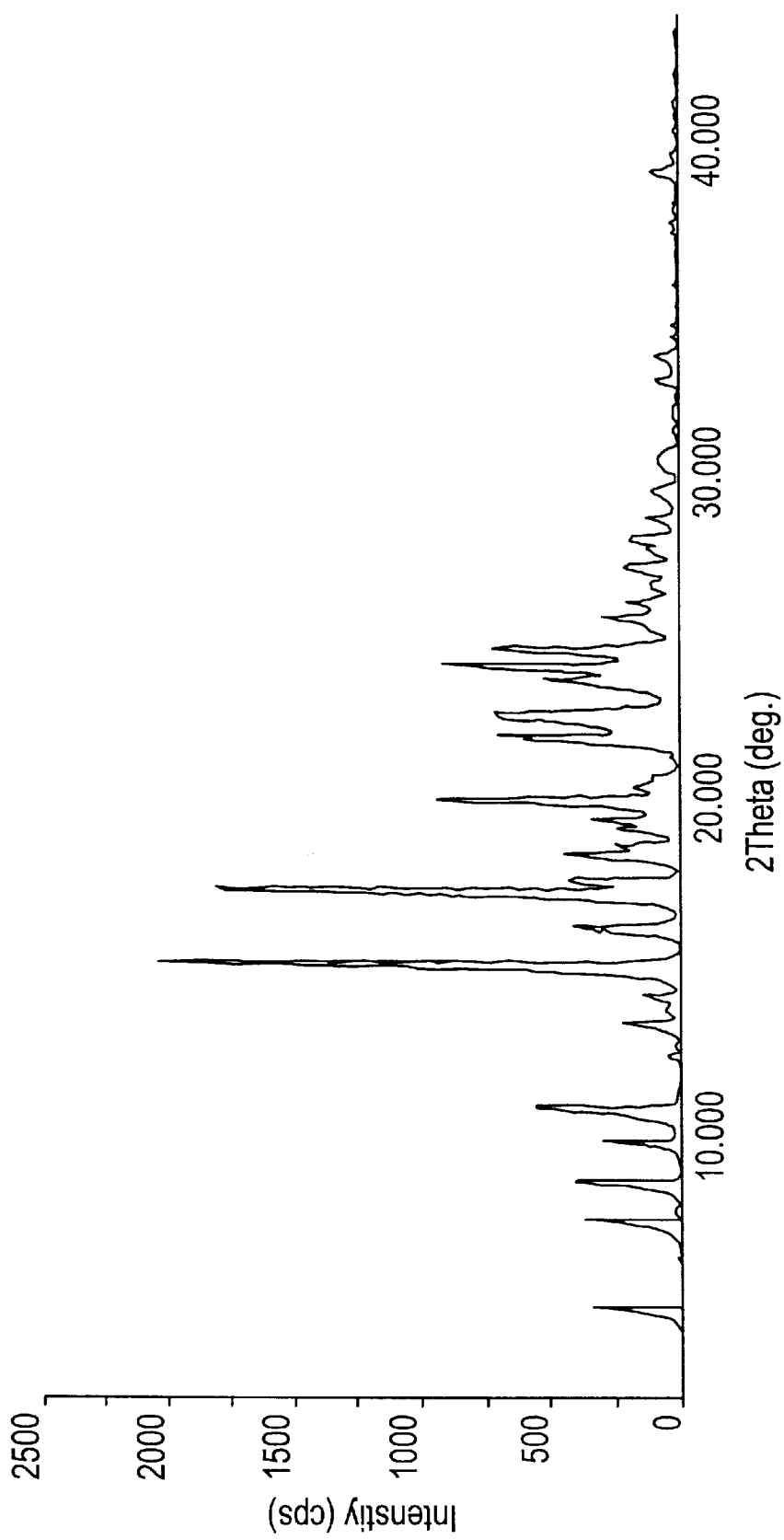

FIG. 5C

| Peak No. | 2Theta | FWHM | d-value | Intensity | I/Io |
|---|---|---|---|---|---|
| 1 | 5.760 | 0.165 | 15.3307 | 344 | 17 |
| 2 | 8.540 | 0.165 | 10.3454 | 540 | 27 |
| 3 | 9.660 | 0.188 | 9.1483 | 392 | 19 |
| 4 | 10.880 | 0.165 | 8.1250 | 295 | 14 |
| 5 | 11.520 | 0.188 | 7.6750 | 195 | 10 |
| 6 | 11.800 | 0.188 | 7.4935 | 546 | 27 |
| 7 | 14.340 | 0.165 | 6.1714 | 210 | 10 |
| 8 | 15.180 | 0.165 | 5.8318 | 138 | 7 |
| 9 | 16.100 | 0.188 | 5.5005 | 2036 | 100 |
| 10 | 17.200 | 0.165 | 5.1512 | 290 | 14 |
| 11 | 17.340 | 0.188 | 5.1099 | 401 | 20 |
| 12 | 18.390 | 0.188 | 4.8230 | 1793 | 88 |
| 13 | 18.740 | 0.235 | 4.7312 | 422 | 21 |
| 14 | 19.480 | 0.212 | 4.5531 | 436 | 21 |
| 15 | 19.780 | 0.165 | 4.4847 | 250 | 12 |
| 16 | 20.240 | 0.165 | 4.3838 | 247 | 12 |
| 17 | 20.520 | 0.165 | 4.3246 | 332 | 16 |
| 18 | 21.080 | 0.212 | 4.2110 | 936 | 46 |
| 19 | 21.500 | 0.235 | 4.1297 | 181 | 9 |
| 20 | 21.860 | 0.235 | 4.0625 | 105 | 5 |
| 21 | 22.940 | 0.188 | 3.8736 | 716 | 35 |
| 22 | 23.620 | 0.376 | 3.7636 | 711 | 35 |
| 23 | 24.700 | 0.188 | 3.6014 | 509 | 25 |
| 24 | 25.120 | 0.235 | 3.5421 | 913 | 45 |
| 25 | 25.660 | 0.259 | 3.4688 | 716 | 35 |
| 26 | 26.300 | 0.141 | 3.3858 | 125 | 6 |
| 27 | 26.680 | 0.165 | 3.3385 | 301 | 15 |
| 28 | 27.200 | 0.259 | 3.2758 | 198 | 10 |
| 29 | 27.600 | 0.188 | 3.2299 | 108 | 5 |
| 30 | 27.780 | 0.118 | 3.2087 | 112 | 5 |
| 31 | 28.280 | 0.306 | 3.1531 | 217 | 11 |
| 32 | 28.820 | 0.141 | 3.0953 | 129 | 6 |
| 33 | 29.140 | 0.282 | 3.0620 | 192 | 9 |
| 34 | 29.760 | 0.165 | 2.9996 | 145 | 7 |
| 35 | 30.540 | 0.141 | 2.9247 | 121 | 6 |
| 36 | 30.700 | 0.118 | 2.9099 | 111 | 5 |
| 37 | 31.740 | 0.118 | 2.8168 | 92 | 5 |
| 38 | 33.940 | 0.259 | 2.6391 | 108 | 5 |
| 39 | 34.640 | 0.259 | 2.5874 | 101 | 5 |
| 40 | 40.340 | 0.212 | 2.2339 | 116 | 6 |

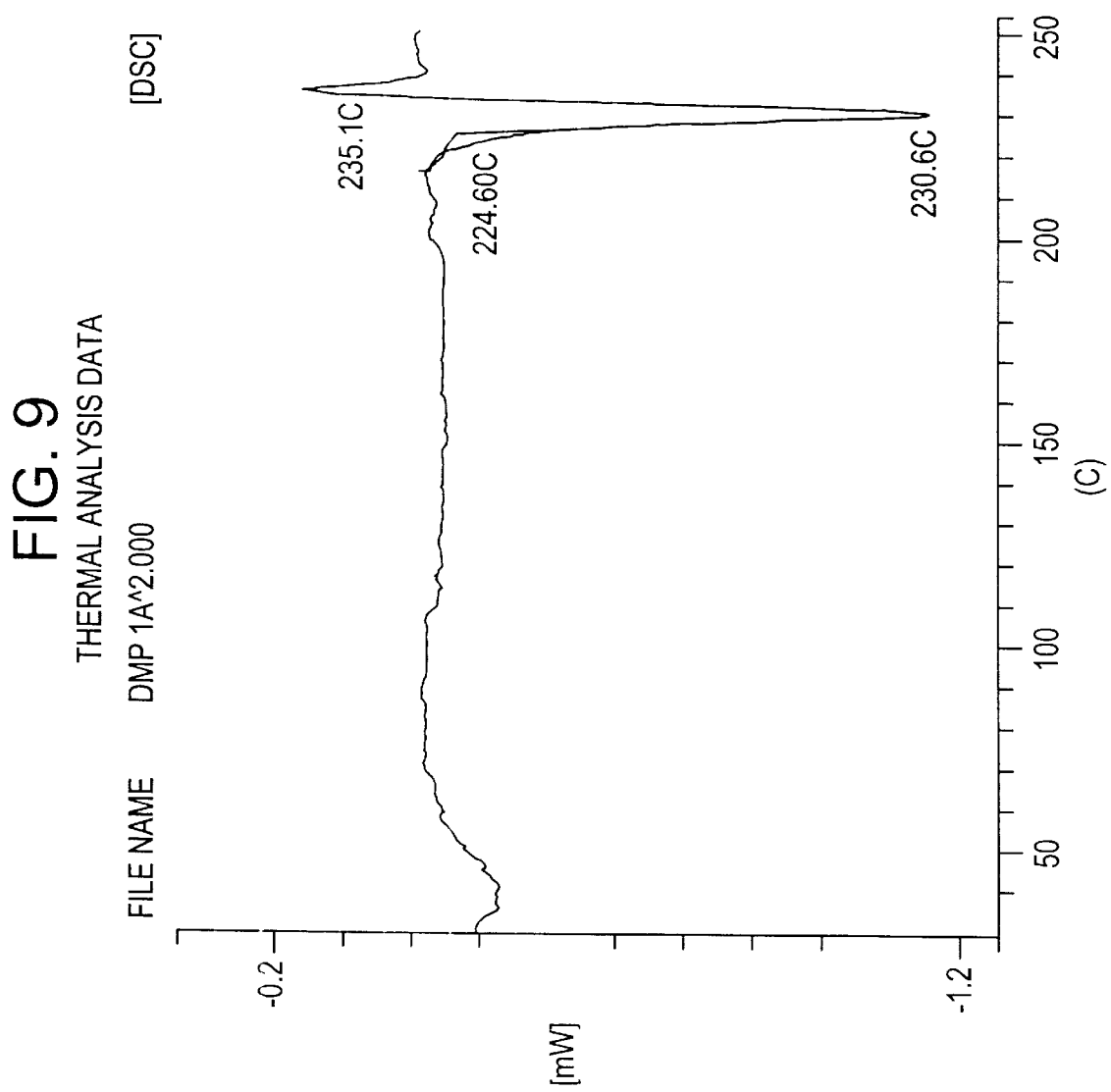

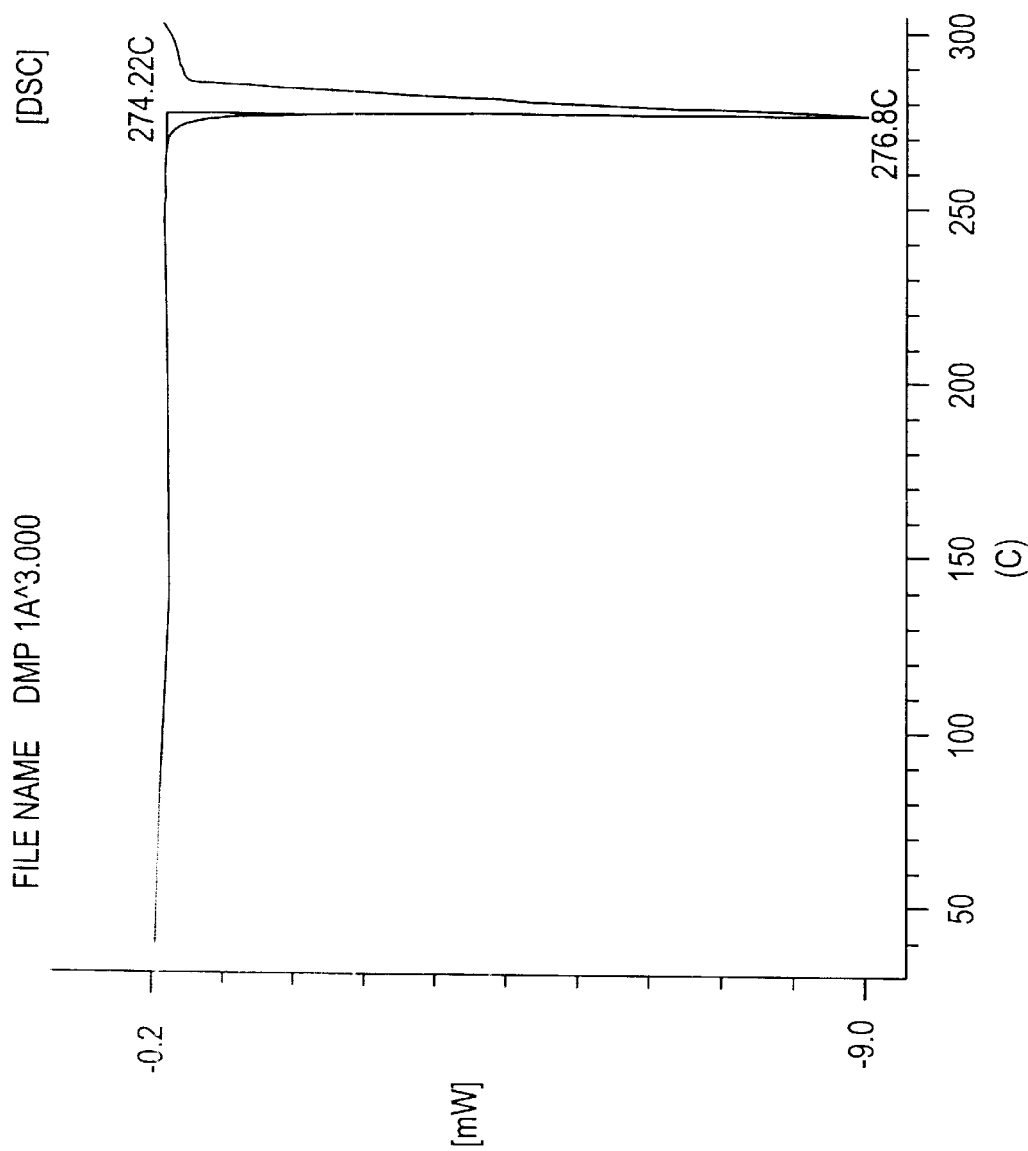

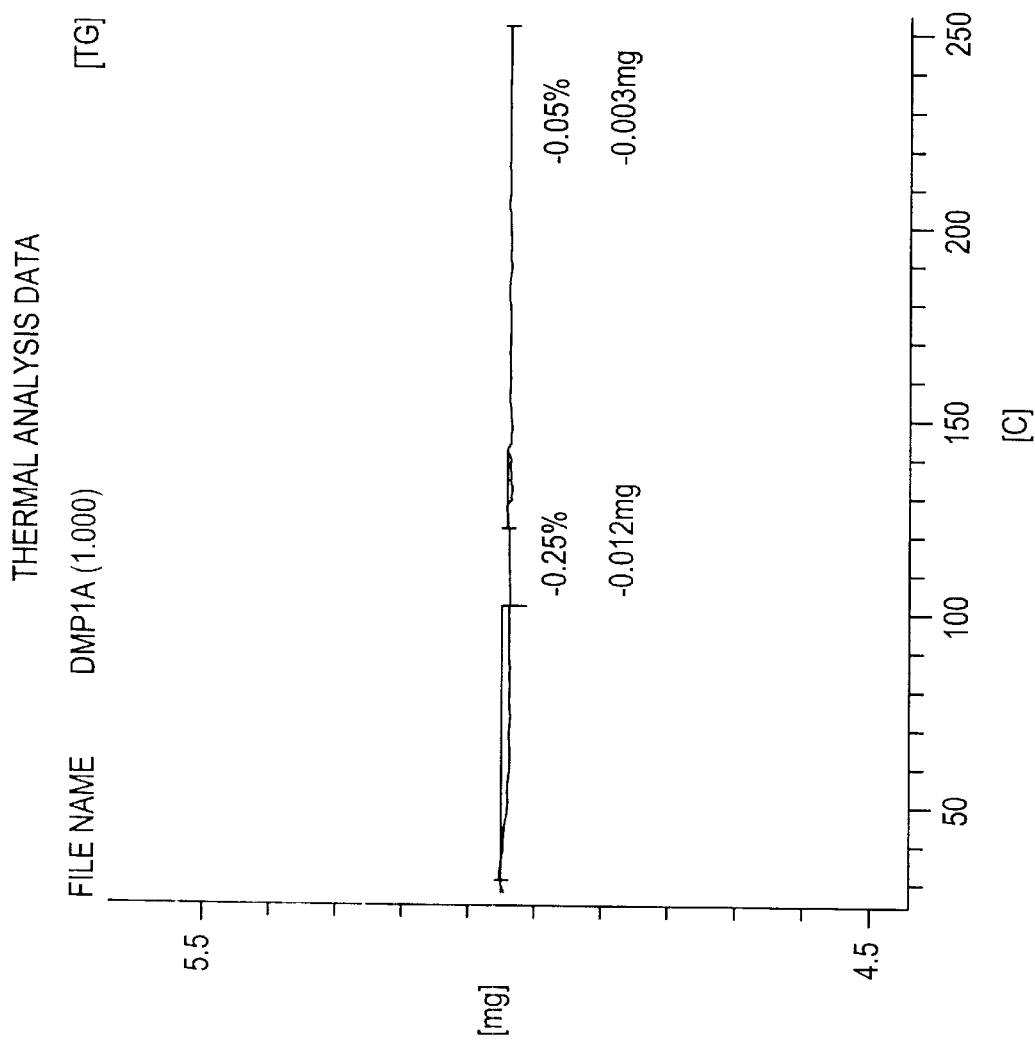

METHODS FOR THE PREPARATION OF POLYMORPHS OF DOXAZOSIN MESYLATE

FIELD OF THE INVENTION

This invention relates to methods for preparing crystalline polymorphic forms of doxazosin mesylate.

BACKGROUND OF THE INVENTION

The compound 1-(4-amino-6, 7-dimethoxy-2-quinazolinyl)-4-[(2,3-dihydro-1,4-benzodioxan-2-yl) carbonyl]piperazine mono methane sulfonate is known by the common name "doxazosin mesylate". Doxazosin mesylate is a pharmaceutically acceptable salt known to be useful in the treatment of hypertension and benign prostatic hyperplasia.

Doxazosin mesylate exists in a number of crystalline polymorphic forms. The Chinese Journal of Medicinal Chemistry (1995, 5:266–270) describes three crystal forms, Form A, Form B and Form C. The article discloses that Form A is obtained by recrystallization of doxazosin mesylate from ethanol; and Forms B and C are produced from recrystallization of doxazosin mesylate from chloroform and water, respectively. Grčman, et al (Farmacevtski vestnik, 1977, 48:292–293) describe Forms A, B, C, D and E of doxazosin mesylate. Grafe and Mörsdorf (CA 02224884, CA 02224916, CA 02225022) disclose methods for the preparation of doxazosin mesylate forms which do not correspond to the polymorphic forms of the present application.

Methods of preparing doxazosin mesylate typically involve dissolving doxazosin base in solvents such as chloroform and dimethylformamide. Difficulties in removing all the solvent from the precipitate may result in a final formulation that contains pharmacologically impermissible levels of the solvent that are toxic and that may adversely effect the activity of the doxazosin mesylate.

Therefore, methods of preparing Forms A and D doxazosin mesylate using solvents that are readily removed from the doxazosin mesylate residue and do not impose problems of pharmacological toxicity are highly desirable.

SUMMARY OF THE INVENTION

In accordance with the present invention, a process for the preparation of Form D doxazosin mesylate is provided, which comprises:
  (a) dissolving doxazosin base and methanesulfonic acid in an alcohol having from 1 to 8 carbon atoms;
  (b) precipitating the Form D from the resulting solution; and
  (c) separating the Form D doxazosin mesylate product.
In a preferred embodiment, the solvent is methanol.

In another aspect, the present invention provides a process for the preparation of Form A of doxazosin mesylate, which comprises:
  (a) dissolving doxazosin base and methanesulfonic acid in an alcohol having from 1 to 8 carbon atoms, a halohydrocarbon selected from the group consisting of dichloromethane, chloroform and trichloroethane, or mixtures thereof;
  (b) precipitating the Form A from the resulting solution; and
  (c) separating the Form A doxazosin mesylate product.
In a preferred embodiment, the solvent is methanol.

In accordance with a further aspect of the invention, a process is provided for converting Form D doxazosin mesylate to Form A, which comprises:
  (a) dissolving Form D and a solvent mixture of a lower alcohol having from 1 to 8 carbon atoms and a halohydrocarbon selected from the group consisting of chloroform, dichloromethane, 1,2-dichloroethane and trichloroethane;
  (b) precipitating the Form A from the resulting solution; and
  (c) separating the Form A doxazosin mesylate product.

BRIEF DESCRIPTION OF THE DRAWINGS

FIG. 1: Differential scanning calorimetric thermograms (overlay) of anhydrous Form D doxazosin mesylate.

FIG. 2: Differential scanning calorimetric thermograms (overlay) of anhydrous Form A doxazosin mesylate.

FIGS. 3a, 3b, 3c: X-ray powder diffraction analysis of Form D doxazosin mesylate. FIGS. 3a and 3b show the X-ray powder diffraction pattern; FIG. 3c shows X-ray powder diffraction data.

FIGS. 5a, 5b and 5c: X-ray powder diffraction analysis of Form A doxazosin mesylate. FIGS. 5a and 5b show the X-ray powder diffraction pattern; FIG. 5c shows X-ray powder diffraction data.

FIG. 9: Differential scanning calorimetric thermogram of heating of Form D doxazosin mesylate to 250° C.

FIG. 10: Differential scanning calorimetric thermogram of heating of Form D doxazosin mesylate to 300° C.

FIG. 11: Differential scanning calorimetric thermogram of heating of Form D doxazosin mesylate to 250° C.

DETAILED DESCRIPTION OF THE INVENTION

Figure 3A:
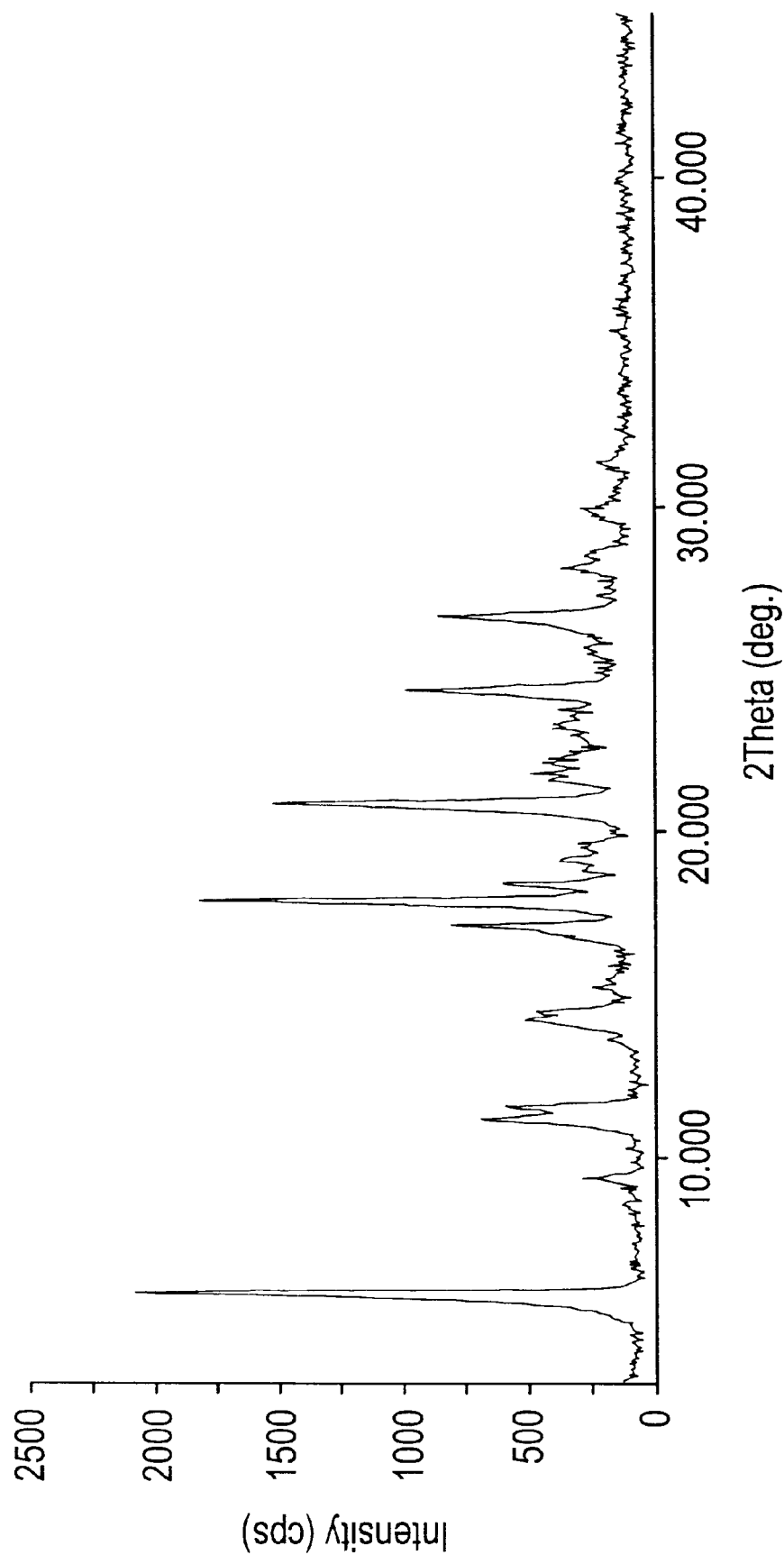
Figure 3B:
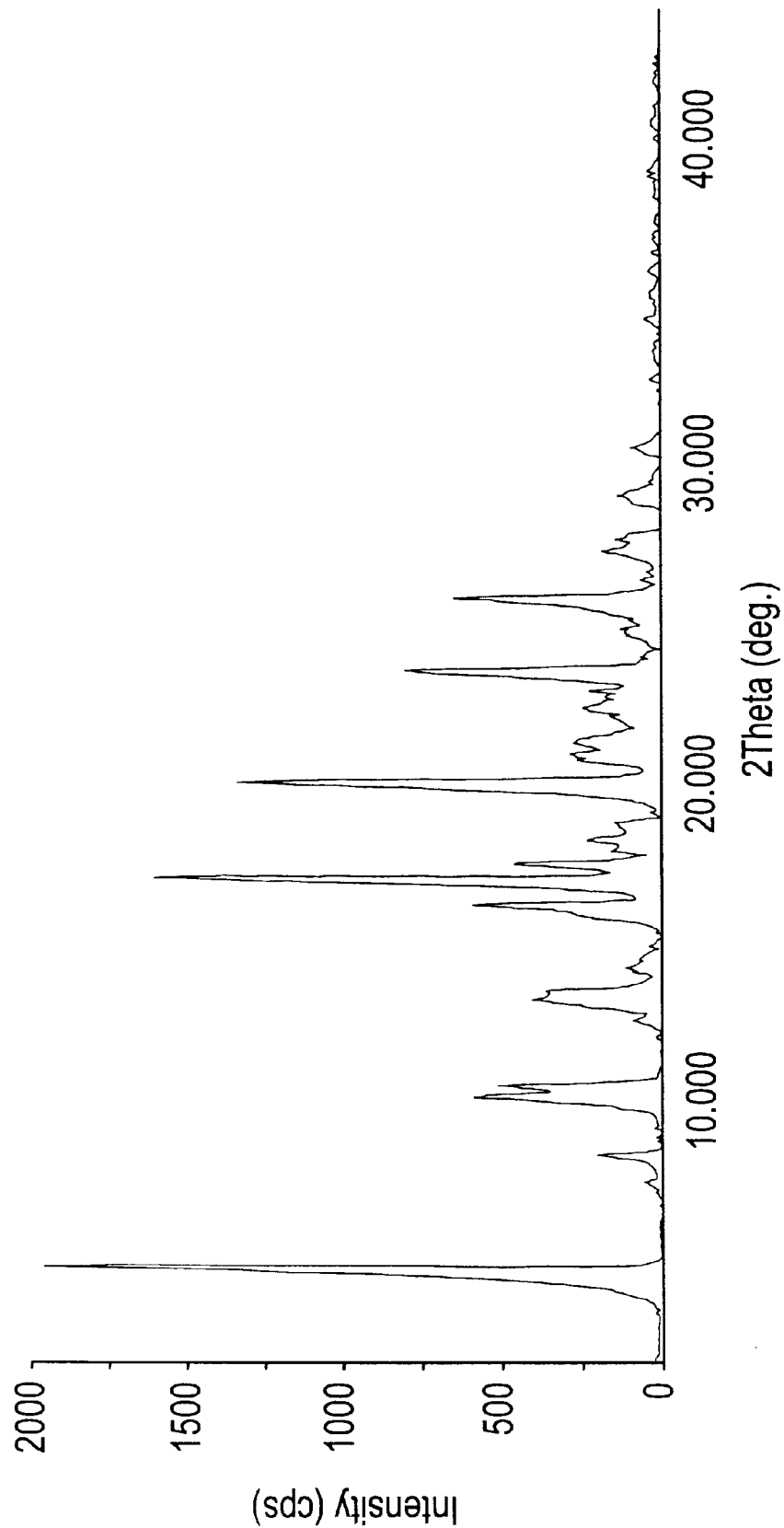
Figure 4:
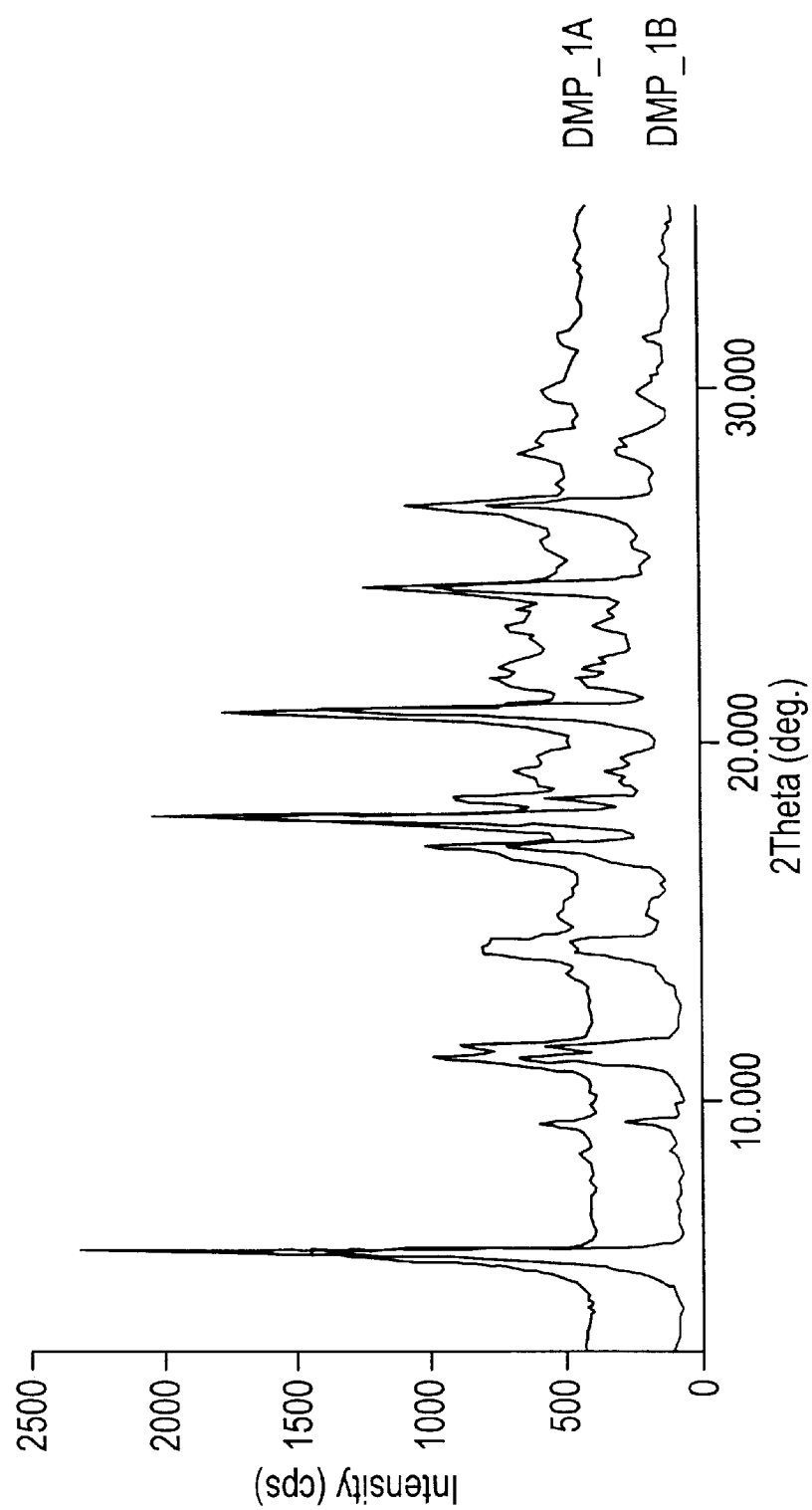
FIG. 4: X-ray powder diffraction patterns (overlay) of anhydrous Form D doxazosin mesylate.
Figure 5A:
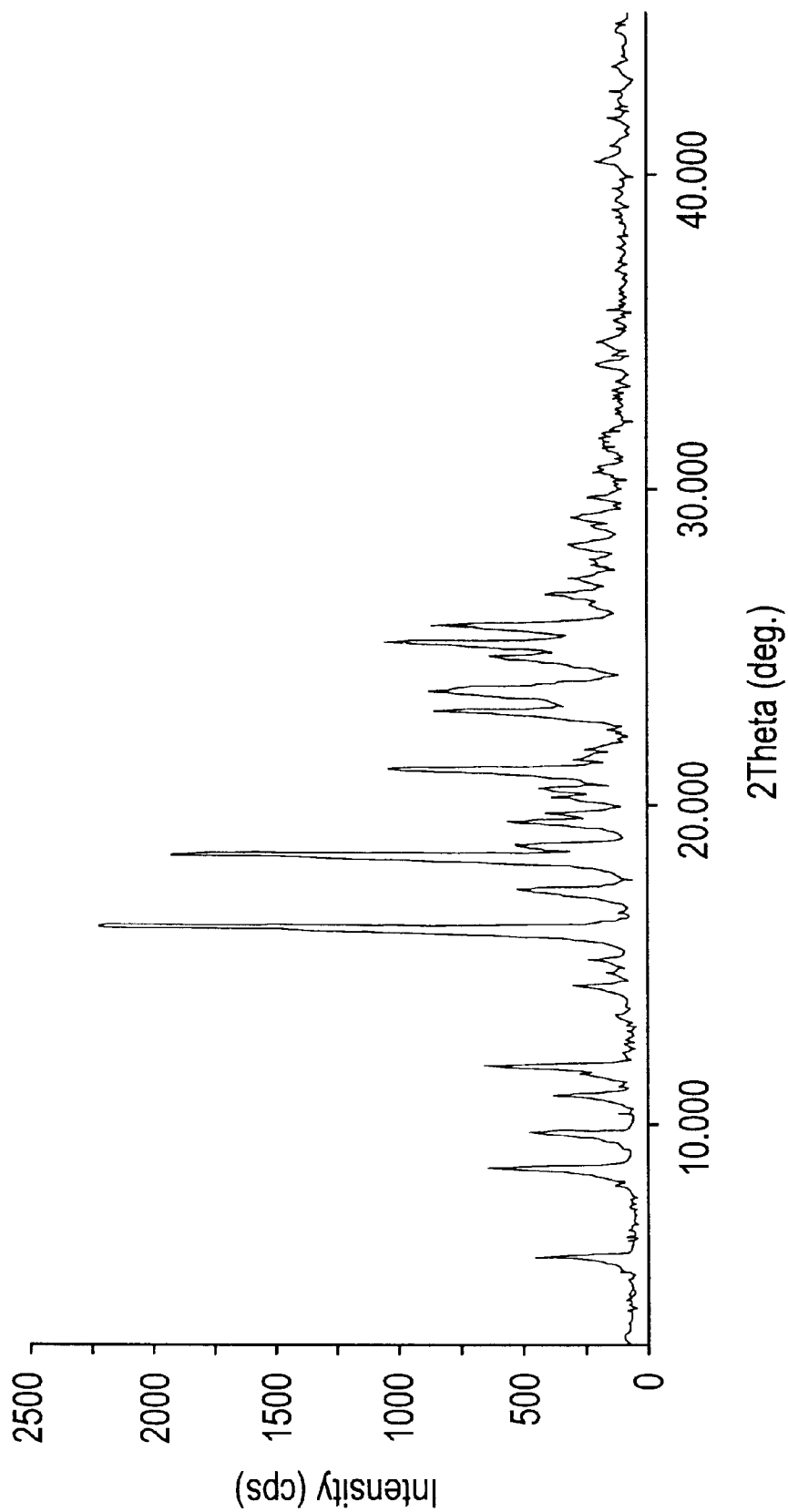

The present invention provides a method of preparing Form D doxazosin mesylate. Form D is obtained by crystallization.

Accordingly, the present invention provides a process for the preparation of Form D doxazosin mesylate from 1-(4-amino-6,7-dimethoxy-2-quinazolinyl)-4-[2,3-dihydro-1,4-benzodioxan-2-yl)carbonyl]piperazine ("doxazosin base") and methane sulfonic acid which method comprises:
  a. dissolving doxazosin base with methane sulfonic acid in an organic solvent;
  b. stirring the reaction solution of step (a) for about 30 minutes to 10 hours at a temperature of about 15–70° C., producing a precipitate of Form D doxazosin mesylate in the reaction solution;
  c. collecting the precipitated Form D doxazosin mesylate formed in step (b).
The solvents employed in this process are alcohols consisting of 1–8 carbon atoms (preferably 1 to 3), and may be selected from isopropyl alcohol, ethanol, methanol, and alkoxy alcohol. In a preferred embodiment the solvent is methanol. Optionally, the reaction mass may further be seeded with a sample of Form D.

Optionally, in the precipitation step, in order to facilitate the precipitation of the doxazosin polymorph, an aprotic polar solvent may be added to the doxazosin and methane sulphonic acid mixture. Examples of suitable aprotic, polar organic solvents include N-methyl-2-pyrrolidone and N,N-dimethylformamide.

The reaction is performed preferably at a temperature of between about 15° to 40° C. Preferably the reaction is performed at about 25° to 35° C. Typically, the reaction time is from about 4 to 6 hours. The precipitate may be collected by filtration, either by gravity or suction. The product may be washed at least one time with solvent before drying. The precipitate may be dried at room temperature or at elevated temperature and/or in vacuo to obtain the final Form D doxazosin mesylate product. For example, the precipitate may be dried, with occasional stirring, at about 60° to 70° C., until the precipitate maintains a constant weight.

The present invention further provides a method of preparing Form A doxazosin mesylate. Form A is obtained either by crystallization or by conversion from Form D.

Accordingly, the present invention provides a process for the preparation of Form A doxazosin mesylate from doxazosin base and methane sulfonic acid which method comprises:

a. dissolving doxazosin base with methane sulfonic acid in an organic solvent or mixture of solvents;

b. stirring the reaction solution of step (a) for about 30 minutes to 10 hours at a temperature of about 15–70° C., producing a precipitate of Form A doxazosin mesylate in the reaction solution;

c. collecting the precipitated Form A doxazosin mesylate formed in step (b).

The precipitate may be collected by filtration, either by gravity or suction. The product may be washed at least one time with solvent before drying. The precipitate may be dried at room temperature or at elevated temperature and/or in vacuo to obtain the final Form A doxazosin mesylate product. For example, the precipitate may be dried at about 60° to 70° C., with occasional stirring, until the precipitate maintains a constant weight.

The methods of the invention may further comprise the step of seeding the reaction solutions of step (a) with the corresponding desired doxazosin mesylate polymorph.

The solvents employed for the preparation of Form D and A are alcohols having 1 to 8 carbon atoms, preferably 1 to 3 carbon atoms, and may include ethanol, isopropanol, methanol and alkoxy alcohol, and halogenated hydrocarbons which may include dichloromethane, 1,2-dichloroethane, chloroform and trichloroethane; or a mixture of any thereof. In preferred embodiments, the solvent is methanol.

Typically, the temperature of the reaction is at about 15° to 40° C. Preferably, the reaction is carried out at room temperature, i.e., 25–35° C. The reaction may be left overnight. Typically, the reaction time is about 5 hours.

Optionally, in the precipitation step, in order to facilitate the precipitation of the doxazosin polymorph, an aprotic polar solvent may be added to the doxazosin and methane sulphonic acid mixture. Examples of suitable aprotic, polar organic solvents include N-methyl-2-pyrrolidone and N,N-dimethylformamide.

In another aspect, the invention provides a method of converting Form D doxazosin mesylate to Form A doxazosin mesylate, which method comprises:

a. dissolving Form D doxazosin mesylate in a solvent;

b. heating the reaction solution of step (a);

c. precipitating Form A from the reaction solution; and d. collecting the precipitated Form A doxazosin mesylate. Typically, the mixture is heated to reflux. The reaction may optionally be stirred during heating to reflux.

Typically, the doxazosin mesylate is precipitated, after heating in step b, by optionally filtering the mixture to remove any undissolved material, then distilling the solution and cooling the filtrate to obtain a precipitate. The mixture is filtered and dried to obtain Form A doxazosin mesylate. The precipitate may be collected by filtration, either by gravity or suction. The product may be washed at least one time with solvent before drying. The precipitate may be dried, as described above, at room temperature or at elevated temperature and/or in vacuo to obtain the final Form A doxazosin mesylate product.

The solvent used for the conversion of Form D to Form A is an alcohol, such as ethanol or methanol, or a halohydrocarbon such as chloroform or a mixture thereof. In a preferred embodiment, the solvent is a mixture of chloroform and methanol.

In the preparation of the doxazosin mesylate polymorphs described herein, the molar ratio of the amount of doxazosin base to methane sulfonic acid is about 1:1.1, preferably about 1:1.0.

In the preparation of the doxazosin mesylate polymorphs described herein, the ratio of the amount of doxazosin to solvent is about 1:8–12, preferably about 1:10.

Generally, the total time for completion of the synthesis of the polymorphs is about 1 to 24 hours. Typically, after an initial clear dissolution, a precipitate is seen at about 10 to 30 minutes after the methane sulfonic acid is added, however longer times are possible.

The polymorphs described herein are characterized by their X-ray diffraction patterns, their infrared spectra and their differential scanning calorimetric thermograms.

EXAMPLES

The present invention will be explained in more detail with reference to the following examples, which are provided by way of illustration only and should not be construed to limit the scope of the invention.

Example 1

Synthesis of Form D

1A: Methane sulfonic acid (59,75 g) was added to a stirred mixture of 1-(4-amino-6,7-dimethoxy-2-quinazolinyl)-4-[(2,3-dihydro-1,4-benzodioxan-2-yl)carbonyl]piperazine (255 g) and methanol (2040 ml). A clear dissolution was observed, followed by the precipitation of the product within 10 to 15 minutes. The reaction mass was stirred at 26–27° C. for six hours. The product was collected by filtration, washed with methanol (250 ml), and dried to obtain Form D (265 g) doxazosin mesylate.

1B: Methane sulfonic acid (2.24 g) was added to a stirred mixture of 1-(4-amino-6,7-dimethoxy-2-quinazolinyl)-4-[2,3-dihydro-1,4-benzodioxan-2-yl)carbonyl]piperazine (10 g) and ethanol (250 ml). A seeding sample of Form D (0.3 g, obtained from example 1A) was added after a clear dissolution was observed. The product was precipitated within 10 to 15 minutes. The reaction mass was stirred at 30–31° C. for five hours. The product was collected by filtration, washed with methanol (35 ml), and dried to obtain Form D (10.9 g) doxazosin mesylate.

Example 2

Synthesis of Form A

2A: Methane sulfonic acid (28 g) was added to a stirred mixture of 1-(4-amino-6,7-dimethoxy-2-quinazolinyl)-4-[2,3-dihydro-1,4-benzodioxan-2yl) carbonyl]piperazine (125 g) and ethanol (3250 ml). A clear dissolution was observed followed by the precipitation of the product within 20 to 30 minutes. The reaction mass was stirred at 31–32° C. for four hours. The product was collected by filtration, washed with ethanol (150 ml), and dried to obtain Form A (137 g) doxazosin mesylate.

2B: Methane sulfonic acid (2.24 g) was added to a stirred mixture of 1-(4-amino-6,7-dimethoxy-2-quinazolinyl)-4-[2,3-dihydro-1,4-benzodioxan-2yl) carbonyl]piperazine (10 g) and dichloromethane (50 ml). A clear dissolution was observed followed by the precipitation of the product within 60 to 90 minutes. The reaction mass was left overnight. The product was collected by filtration, washed with methanol (50 ml), and dried to obtain Form A (9.9 g) doxazosin mesylate.

2C: Methane sulfonic acid (2.24 g) was added to a stirred mixture of 1-(4-amino-6,7-dimethoxy-2-quinazolinyl)-4-[2,3-dihydro-1,4-benzodioxan-2yl) carbonyl]piperazine (10 g), isopropanol (30 ml) and methanol (90 ml). A seeding sample of Form A (3.0 g in 15 ml methanol and 5 ml isopropanol) was added after a clear dissolution was observed. The product was precipitated within 10 to 15 minutes. The reaction mass was stirred at 29–30° C. for four hours. The product was collected by filtration, washed with methanol (25 ml), and dried to obtain Form A (12.8 g) doxazosin mesylate.

2D: Methane sulfonic acid (11.2 g) was added to a stirred mixture of 1-(4-amino-6,7-dimethoxy-2-quinazolinyl)-4-[2,3-dihydro-1,4-benzodioxan-2yl) carbonyl]piperazine (50 g), dichloromethane (100 ml) and methanol (35 ml). A seeding sample of Form A (1.6 g) was added after a clear dissolution was observed. The product was precipitated within 20 to 30 minutes. The reaction mass was stirred at 32–34° C. for six hours. The product was collected by filtration, washed with methanol (50 ml), and dried to obtain Form A (38.3 g) doxazosin mesylate.

2E: Methane sulfonic acid (2.24 g) was added to a stirred mixture of 1-(4-amino-6,7-dimethoxy-2-quinazolinyl)-4-[2,3-dihydro-1,4-benzodioxan-2yl) carbonyl]piperazine (10 g) and methanol (80 ml). A seeding sample of Form A (0.3 g) was added after a clear dissolution was observed. The product was precipitated within 10 to 15 minutes. The reaction mass was stirred at 30–31° C. for four hours. The product was collected by filtration, washed with methanol (25 ml), and dried to obtain Form A (10.8 g) doxazosin mesylate.

2F: Conversion of Form D to Form A: 1-)4-amino-6,7-dimethoxy-2-quinazolinyl)-4-[2,3-dihydro-1,4-benzodioxan-2yl) carbonyl]piperazine monomethane sulfonate (10 g, prepared as for the procedure in example-1A) was added portionwise to a stirred mixture of dichloromethane (40 ml) and methanol (20 ml) at reflux. A clear solution was obtained in about 15 minutes. It was filtered to remove undissolved material, if any. The filtrate was distilled to a minimum volume and cooled until a solid was separated. The solid was collected by filtration and dried to yield Form A (7.8 g) doxazosin mesylate.

Example 3
Characterization of Forms A and D

The differential scanning calorimetric (DSC) analysis of the polymprphs produced according to the methods described herein was carried out on a Shimadzu DSC-50 instrument. The thermograms were recorded under nitrogen atmosphere at a heating rate of 10° C./min. The powder XRD diffractograms were obtained from Rigaku D/Max-2200 diffractometer with copper Kα (λ=1.5418 A) radiation source (50 kV, 34 mA). The samples were scanned from 3 to 45 degrees (2θ) with a scan speed of 3 degrees/min. Samples were gently crushed prior to the measurement to reduce particle size effects on the peak intensities. The FTIR spectra of the samples were recorded on a Perkin-Elmer 1650 FT-IR spectrophotometer as the solid state as dispersion in a KBr pellet which were pressed at ~10 tons.

The DSC thermogram of Form D displayed endo-exo-endo pattern (FIG. 1). The sample was heated to 250° C. in DSC (FIG. 9) and cooled and then heated to 300° C. (FIG. 10). The first endo-exotherms disappeared in the rerun. The thermogravimetry (TG) experiment (FIG. 11) did not reveal any weight loss. The endo-exo pattern may be attributed to phase transition.

The DSC thermogram of Form A displayed a single melting endotherm at 270° C. (FIG. 2), unlike Form D. The X-ray data of this form differed from those of Form D. This sample was heated to 250° C., cooled to room temperature, and reheated to 300° C. in DSC. The XRD and DSC thermogram indicated no change, ruling out any insignificant transformation due to heating.

Figure 6:
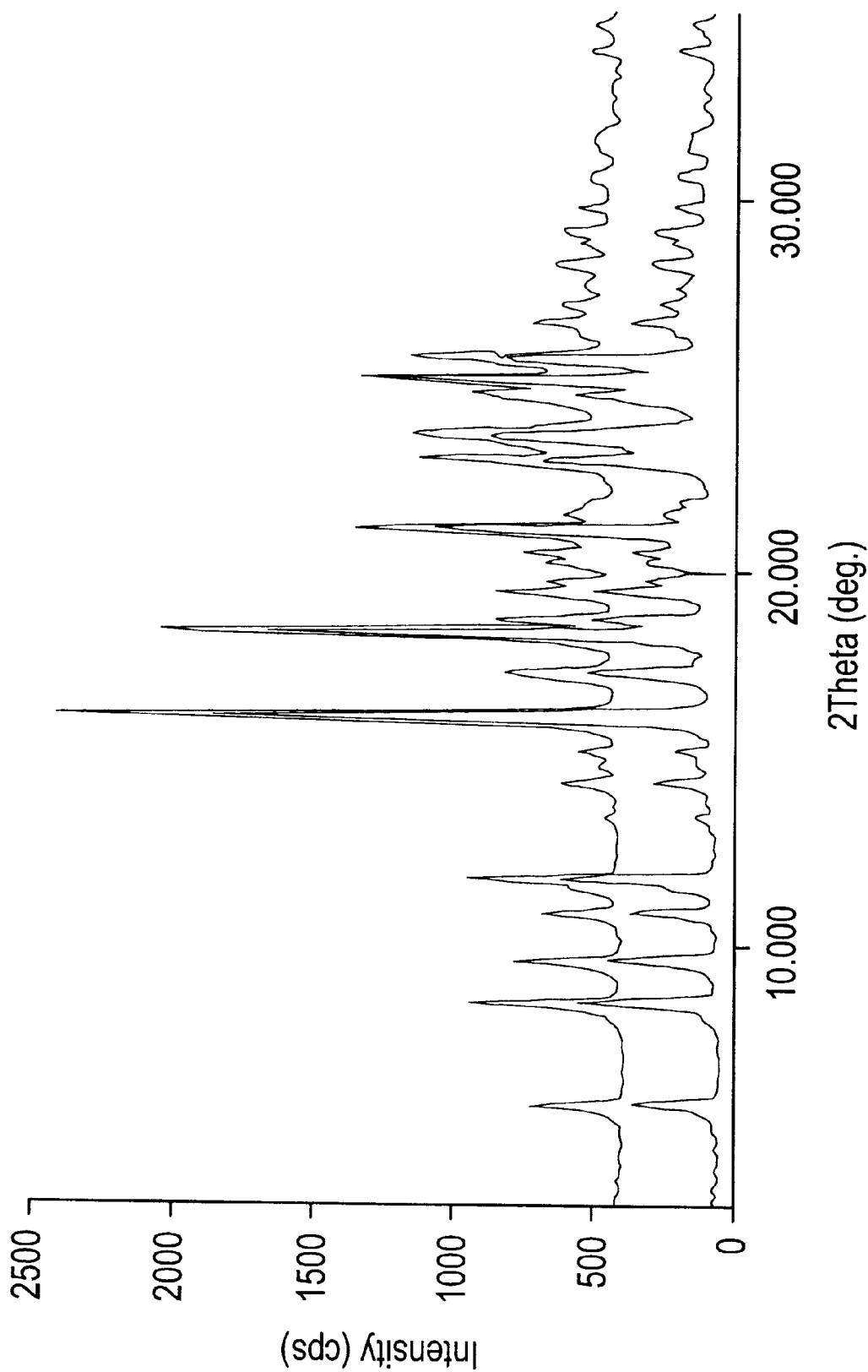
FIG. 6: X-ray powder diffraction patterns (overlay) of anhydrous Form A doxazosin mesylate.
Figure 7:
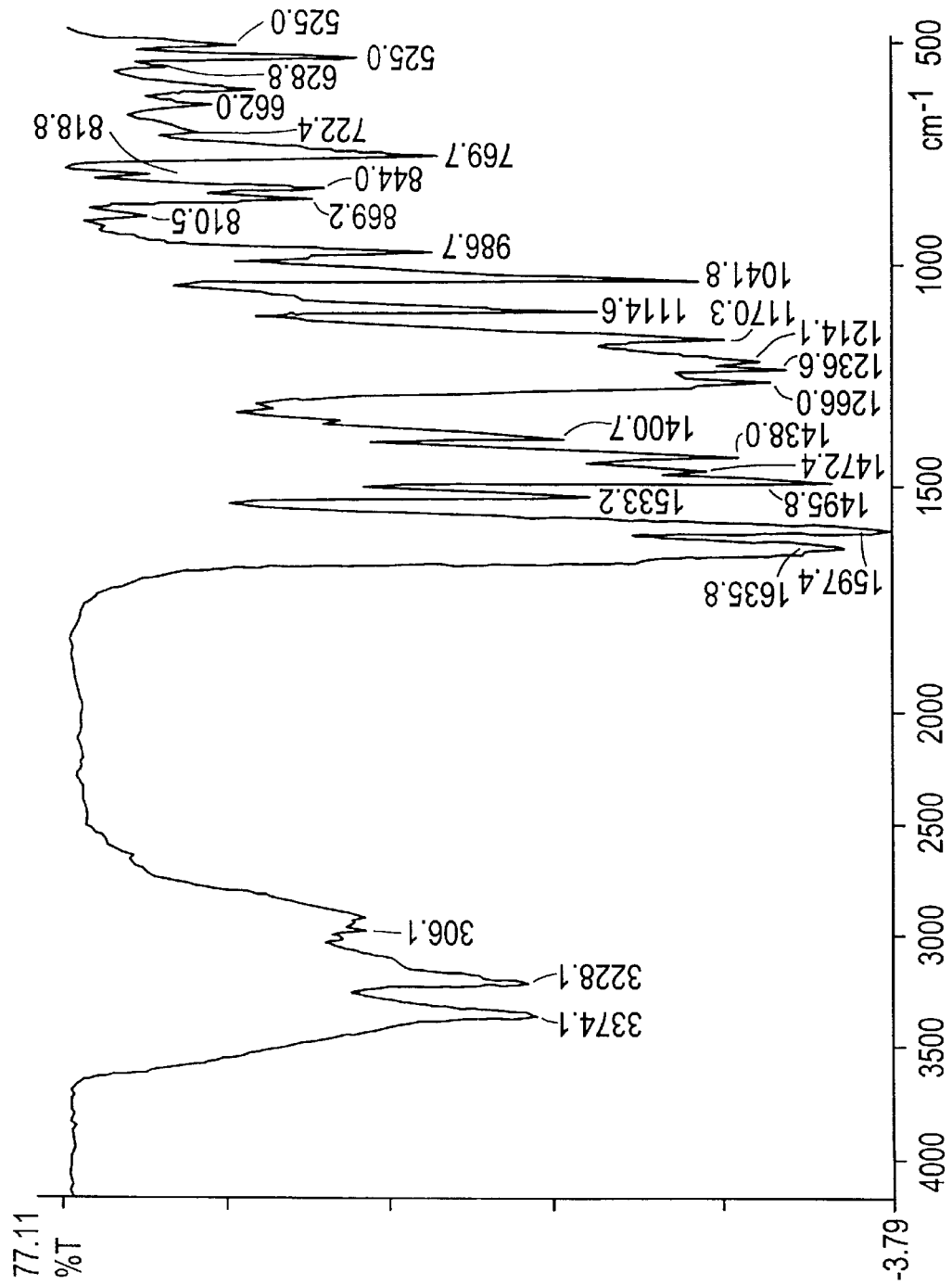
FIG. 7: Infrared spectrum of anhydrous Form D doxazosin mesylate.
Figure 8:
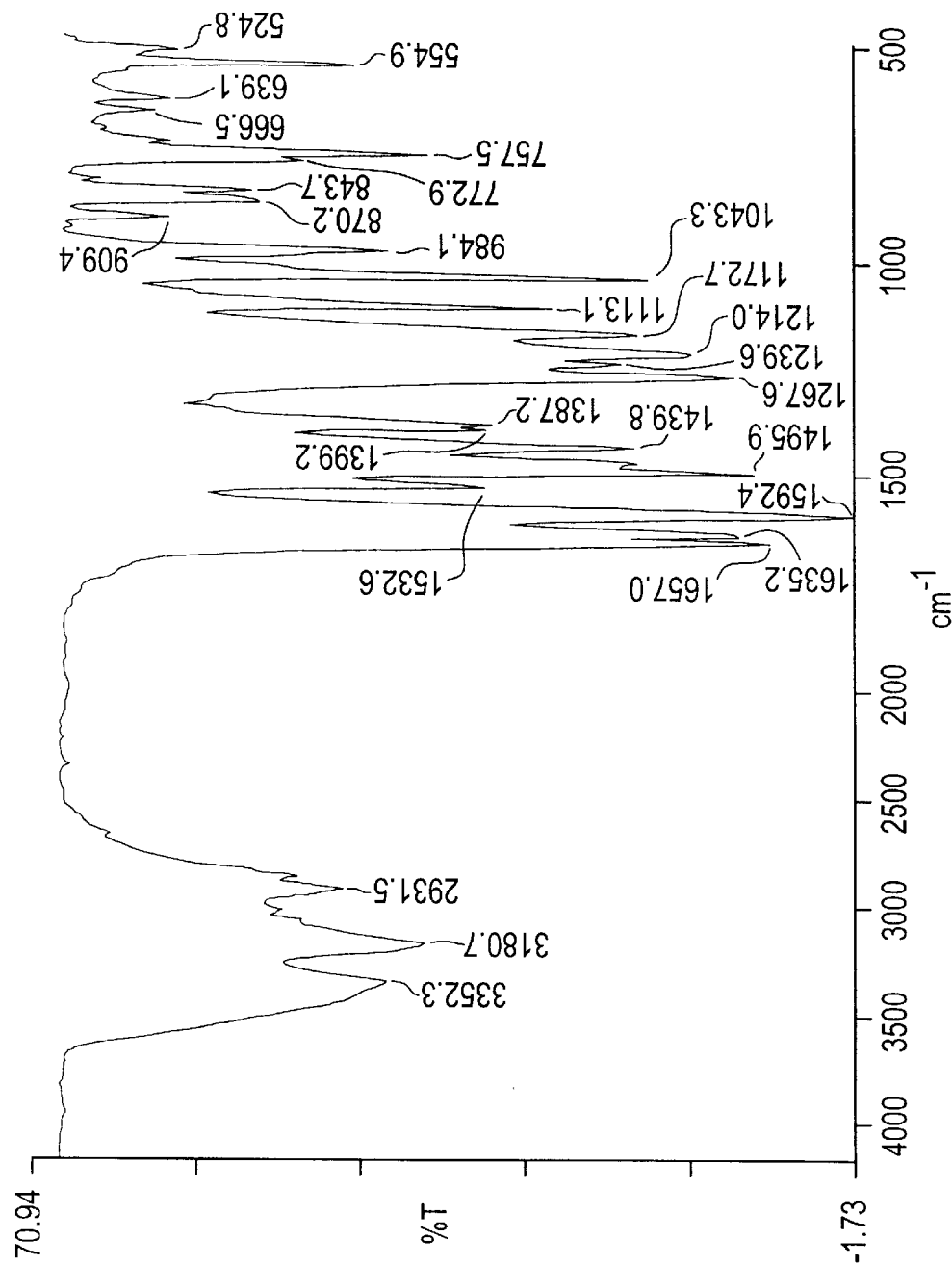
FIG. 8: Infrared spectrum of anhydrous Form A doxazosin mesylate.

Careful examination of the FTIR spectra of Forms A (FIG. 8) and D (FIG. 6) revealed the following differences:

a. while significant peaks were present at 2931 $cm^{-1}$ in Form A, Form D had only small noise in this region.

b. the intensity of the peak at 1657 $cm^{-1}$ was stronger in Form A, while it appeared as a shoulder in Form D.

c. the peaks at 1239 $cm^{-1}$ and 1218 $cm^{-1}$ appeared in equal intensities in Form D. In Form A, the intensity of peak at 1218 $cm^{-1}$ was more than that of the peak at 1239 $cm^{-1}$.

d. In Form D the peak at 757 $cm^{-1}$ was seen as a shoulder next to the peak at 773 $cm^{-1}$. The peak at 773 $cm^{-1}$ resolved from 757 $cm^{-1}$ in Form A.

The position (2θ) of intense peaks of the polymorphs are tabulated with their I/Io ratio in Table 1.

TABLE 1

| Form D | | Form A | |
| --- | --- | --- | --- |
| 2θ | (I/Io) | 2θ | (I/Io) |
| 5.7 | 100 | 5.8 | 17 |
| 17.1 | 31 | 8.5 | 27 |
| 17.8 | 83 | 9.7 | 19 |
| 18.4 | 24 | 10.9 | 17 |
| 20.8 | 68 | 11.8 | 27 |
| 24.3 | 41 | 16.1 | 100 |
| 26.6 | 33 | 18.4 | 88 |
| — | — | 21.1 | 46 |
| — | — | 25.1 | 45 |

What is claimed is:

1. A method for the preparation of Form D of doxazosin mesylate which comprises:

(a) dissolving doxazosin base and methane sulfonic acid in an alcohol having from 1 to 8 carbon atoms;

(b) precipitating Form D of doxazosin mesylate from the resulting solution; and (c) separating the Form D of doxazosin mesylate.

2. Form D of doxazosin mesylate have X ray diffraction (2θ) values 5.7, 17.1, 17.8, 18.4, 20.8, 24.3, 26.6.